United States Patent
Mackie et al.

(10) Patent No.: US 6,636,622 B2
(45) Date of Patent: *Oct. 21, 2003

(54) METHOD AND APPARATUS FOR CALIBRATION OF RADIATION THERAPY EQUIPMENT AND VERIFICATION OF RADIATION TREATMENT

(75) Inventors: Thomas R. Mackie, Madison, WI (US); Paul J. Reckwerdt, Madison, WI (US); Todd R. McNutt, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/038,379

(22) Filed: Jan. 4, 2002

(65) Prior Publication Data

US 2002/0080912 A1 Jun. 27, 2002

Related U.S. Application Data

(63) Continuation of application No. 08/950,462, filed on Oct. 15, 1997, now Pat. No. 6,345,114, which is a continuation of application No. 08/490,184, filed on Jun. 14, 1995, now abandoned.

(51) Int. Cl.[7] ................................................ G06K 9/00
(52) U.S. Cl. ........................ 382/132; 378/145; 378/411
(58) Field of Search ............................... 382/128–134; 250/390.02, 390.03; 378/21, 65, 74, 76, 145–151, 140, 208, 207; 600/1, 3, 411, 300, 407

(56) References Cited

U.S. PATENT DOCUMENTS

| | | | | |
|---|---|---|---|---|
| 4,455,609 A | * | 6/1984 | Inamura et al. | 250/370.07 |
| 4,868,399 A | | 9/1989 | Sephton | |
| 4,868,843 A | * | 9/1989 | Nunan | 250/505.1 |
| 5,025,376 A | | 6/1991 | Bova et al. | |
| 5,138,647 A | * | 8/1992 | Nguyen et al. | 378/189 |
| 5,317,616 A | | 5/1994 | Swerdloff et al. | |
| 5,394,452 A | | 2/1995 | Swerdloff et al. | |
| 5,418,715 A | | 5/1995 | Deasy | |
| 5,442,675 A | | 8/1995 | Swerdloff et al. | |
| 5,458,125 A | | 10/1995 | Schweikard | |
| 5,528,650 A | | 6/1996 | Swerdloff et al. | |
| 5,548,627 A | | 8/1996 | Swerdloff et al. | |
| 5,596,619 A | * | 1/1997 | Carol | 417/137 |
| 5,621,779 A | | 4/1997 | Hughes et al. | |
| 5,625,663 A | | 4/1997 | Swerdloff et al. | |
| 5,661,773 A | * | 8/1997 | Swerdloff et al. | 378/65 |
| 5,668,371 A | | 9/1997 | Deasy et al. | |
| 5,673,300 A | | 9/1997 | Reckwerdt et al. | |
| 5,724,400 A | | 3/1998 | Swerdloff et al. | |
| 5,754,622 A | | 5/1998 | Hughes | |
| 5,847,403 A | * | 12/1998 | Hughes et al. | 250/505.1 |
| 6,345,114 B1 | | 2/2002 | Mackie et al. | |

FOREIGN PATENT DOCUMENTS

EP 0804943 A2 5/1997

OTHER PUBLICATIONS

Shalev et al., "On–Line Verification of Radiation Treatment Portals", IEEE Engineering in Medicine & Biology Society, IEEE Aug. 1988.*

(List continued on next page.)

*Primary Examiner*—Jayanti K. Patel
(74) *Attorney, Agent, or Firm*—Quarles & Brady LLP

(57) ABSTRACT

A method of calibration and verification of radiotherapy systems deduced radiation beam fluence profiles from the radiation source from a complete model of an extended radiation phantom together with dose information from a portal imaging device. The improved beam fluence profile characterization made with an iterative modeling which includes scatter effects may be used to compute dose profiles in the extended phantom or a patient who has been previously characterized with a CT scan. Deviations from the expected beam fluence profile can be used to detect patient misregistration.

32 Claims, 3 Drawing Sheets

OTHER PUBLICATIONS

Keller, Harald, et al., XP–002106199, Calibration of a portal imaging device for high–precision dosimetry: A Monte Carlo study, Med. Phys. 25:1891–1902 (Oct. 1998).

Hansen, V.N., et al., XP–000592655, The application of transit dosimetry to precision radiotherapy, Medical Physics, 23:712–721 (Feb. 1996).

McNutt, Todd R., et al., XP 000623664, Modeling dose distributions from portal dose images using the convolution/superposition method, Med. Phys. 23:1381–1392, (Aug. 1996).

Shalev, S., et al., On–Line Verification of Radiation Treatment Portals, IEEE Engineering in Medicine & Biology Soc. 10th Annual Int'l Conference, 1988, pp. 382–383.

Entine, G. et al., Recent Results with a CdTe Imaging Portal Scanner for Radiation Therapy, 1993 IEEE Transactions on Nuclear Science, vol. 40, No. 4, Aug. 1993, pp. 1012–1016.

Ying, Xingren, et al., Portal Dose Images II: Patient Dose Estimation, Int'l Journal of Radiation Oncology Biology Physics, vol. 18 No. 6, Jun. 1990, pp. 1465–1475.

Wong, John W., et al., Portal Dose Images I: Quantitative Treatment Plan Verification, Int'l. Journal of Radiation Oncology Biology Physics, vol. 18 No. 6, Jun. 1990, pp. 1455–1463.

Hansen, V.N., et al., Transit Dosimetry–Computer Generated Dose Images for Verification, Proceedings of the XIth Int'l Conf. on the use of Computers in Radiation Therapy. Mar. 20–24, 1994.

Kirby, Michael C., et al., The Use of an Electronic Portal Imaging Decive for Exit Dosimetry and Quality Control Measurements, Int. J. Radiation Oncology Biology Physics, vol. 31, No. 3, pp. 593–603 (1995).

Fiorino, C., et al., Exit Dose Measurements by Portal Film Dosimetry, Italy.

Lewis, D.G., et al., A megavoltage CT scanner for radiotherapy verification, Phys. Med. Biol. 1992, vol. 37, No. 10, pp. 1985–1999.

\* cited by examiner

METHOD AND APPARATUS FOR CALIBRATION OF RADIATION THERAPY EQUIPMENT AND VERIFICATION OF RADIATION TREATMENT

CROSS REFERENCE TO RELATED APPLICATIONS

This application is a continuation of U.S. application Ser. No. 08/950,462 now U.S. Pat. No. 6,345,114, filed Oct. 15, 1997 which is a continuation of U.S. application Ser. No. 08/490,184 filed Jun. 14, 1995 now abandoned.

BACKGROUND OF THE INVENTION

1. Field of the Invention

This invention relates to radiation therapy equipment for the treatment of tumors or the like and specifically to an improved method of characterizing the radiation beam of such systems and confirming the dose received by the patient using a portal image of radiation exiting the patient.

2. Background of the Invention

Medical equipment for radiation therapy treats tumorous tissue with high energy radiation. The dose and the placement of the dose must be accurately controlled to insure both that the tumor receives sufficient radiation to be destroyed, and that damage to the surrounding and adjacent non-tumorous tissue is minimized.

Internal-source radiation therapy places capsules of radioactive material inside the patient in proximity to the tumorous tissue. Dose and placement are accurately controlled by the physical positioning of the isotope. However, internal-source radiation therapy has the disadvantages of any surgically invasive procedure, including discomfort to the patient and risk of infection.

External-source radiation therapy uses a radiation source that is external to the patient, typically either a radioisotope, such as $^{60}$Co, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue may be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also may be reduced by tightly collimating the radiation beam to the general cross section of the tumor taken perpendicular to the axis of the radiation beam. Numerous systems exist for producing such a circumferential collimation, some of which use multiple sliding shutters which, piecewise, may generate a radioopaque mask of arbitrary outline.

The radiation beam may also be controlled by insertion of wedges or blocks into the beam to reduce the intensity or fluence of the beam by means of attenuation in some areas. U.S. Pat. No. 5,317,616 issued May 31, 1994, incorporated by reference and assigned to the same assignee as the present invention, describes a shutter system that provides an alternative to wedges for reducing fluence or intensity portions of the radiation beam by temporally modulating the radiation beam with collimator leaves.

The ability to selectively adjust intensity of individual portions or rays in the radiation beam is essential if the cumulative dose from multiple angles is to be accurately controlled. For example, two exposures along perpendicular directions may be made to expose a generally rectangular area within the patient. In order that the corner of the rectangular area closest to both of the radiation sources at the two angles does not receive a disproportionate radiation dose, wedges are used in each exposure to reduce the beam intensity on the side of the beam closest to the radiation source for the other exposure side. In this way, after the two exposures, a uniform dose has been received by the area.

In order to confirm the positioning of the collimation blades and blocks used in a particular radiation therapy session, a "portal image" may be obtained in which radiation exiting from the patient is recorded on x-ray film or the like. A visual examination of this image provides a poor quality x-ray radiograph that gives a gross indication that the "geometry" of the radiation beam is correct.

Confirmation of the dose received by the patient may be provided by the placement of point dosimeters on the surface of the body or within body cavities.

Developing a plan of radiation treatment involving radiation at multiple angles requires that the dose provided by the beam at each angle be well known. For this reason, it is normal practice to determine the dose distribution in a standard water phantom. The water phantom is generally a water-filled box placed within the radiation beam so that the beam cuts enters the box perpendicularly to the water surface. A small radiation detector, such as an ionization chamber, is physically scanned through the volume of the phantom to make dose measurements. Under the assumption that the phantom material is similar to a human patient, this dose distribution reflects that which may be expected in a human patient if the patient's shape and actual tissue density are neglected.

The measurement of the dose distribution in this manner is time consuming and inaccurate. A change in collimation changes the intensity even along central and uncollimated rays as a result of scatter within the phantom and from the collimator itself. For this reason, a sequence of dose measurements must be made for different beam collimations and for the use of different blocks.

These dose distribution measurements also permit the evaluation of the uniformity of the radiation beam provided by the system, and in particular, the intensity in a cross-section of the radiation beam before it enters the patient (the "beam intensity profile"). If the intensity of the beam deviates beyond a certain amount from a uniform value, adjustments may be made in the alignment of the radiation source and/or filters may be inserted into the radiation beam to improve its intensity profile. Because the beam intensity profile may vary over time, such measurements must be repeated on a regular basis.

Determining the dose distribution within a standard phantom for a variety of the beam sizes and filtrations by scanning a phantom with a dosimeter is time consuming and expensive.

SUMMARY OF THE INVENTION

The present invention provides a method of automatically characterizing the radiation beam of a radiation therapy system (and the dose to a phantom or patient) using the radiation intensity information contained within the portal image. The present invention recognizes that the amount of radiation exiting the patient or phantom, as provided by the portal image, together with knowledge about the composition and geometry of the patient or phantom, can be used to characterize the radiation beam intensity profile irradiating the patient or phantom without independent dose measurements by a scanning dosimeter.

This more accurate characterization of the radiation beam fluence profile may be used to generate other information including: 1) a more accurate determination of the dose received by the patient, 2) a scatter-free portal image that may better confirm the geometry of collimator blades and patient blocks, and 3) a verification that the correct patient volume is being treated.

Specifically, the present invention provides a method of calibrating a radiation therapy machine involving the steps of irradiating a phantom of known composition and geometry with a beam of radiation having a beam intensity profile and acquiring a measured portal image indicating the intensity of the beam of radiation along a number of rays and after it has passed through the phantom. An electronic computer receives the measured portal image as well as the character and composition of the phantom and models an expected portal image based on an irradiation of the phantom with an assumed beam intensity profile. This expected portal image is compared with the measured portal image to produce a correction image which increments or scales the assumed intensity profile in an iterative process. The process converges with the assumed intensity profile measurement equal to the actual intensity profile of the radiation therapy system.

Thus, it is one object of the invention to characterize the beam intensity profile of the radiation source without the need to measure the intensity of the beam prior to the patient or within a phantom.

The accurate characterization of the beam fluence profile may be used to determine a dose distribution throughout the phantom.

Thus, it is another object of the invention to eliminate the time consuming process of measuring dose within a water phantom with a movable dosimeter. Accurate modeling of the primary radiation passing through the phantom permits dose determinations for a variety of collimations and wedges with a single phantom measurement by including scatter contributions after the entire primary radiation has been determined.

The measure of the intensity profile may also be used to develop a simulated scatterless portal image based on modeled irradiation of a phantom without scatter.

Thus, it is another object of the invention to provide an improved version of the traditional portal image for geometric verification. Elimination of scatter produces a sharper image from which it is easier to verify that the patient has been properly treated.

The invention may also be employed where the phantom is replaced by a patient having had a CT scan of the irradiated volume which accurately characterizes the composition and geometry of that volume. In this case, an extremely accurate determination of the dose received by the patient may be obtained.

The foregoing and other objects and advantages of the invention will appear from the following description. In the description, reference is made to the accompanying drawings which form a part hereof and in which there is shown by way of illustration several preferred embodiments of the invention. Such embodiments do not necessarily represent the full scope of the invention, however, and reference must be made therefore to the claims herein for interpreting the scope of the invention.

DETAILED DESCRIPTION OF THE PREFERRED EMBODIMENT

A General Radiation Therapy Unit

Figure 1:
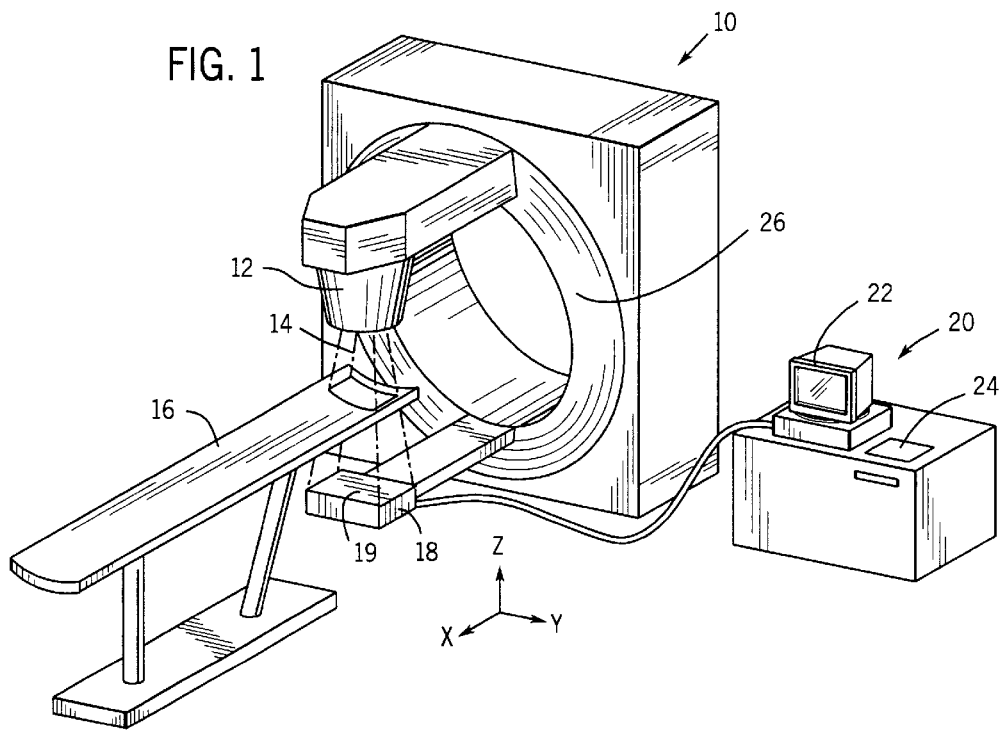
FIG. 1 is a perspective view of a radiation therapy system such as may be used to practice the present invention having a portal imaging device for receiving radiation transmitted through the patient and providing portal image data to an attached computer system.
Figure 2:
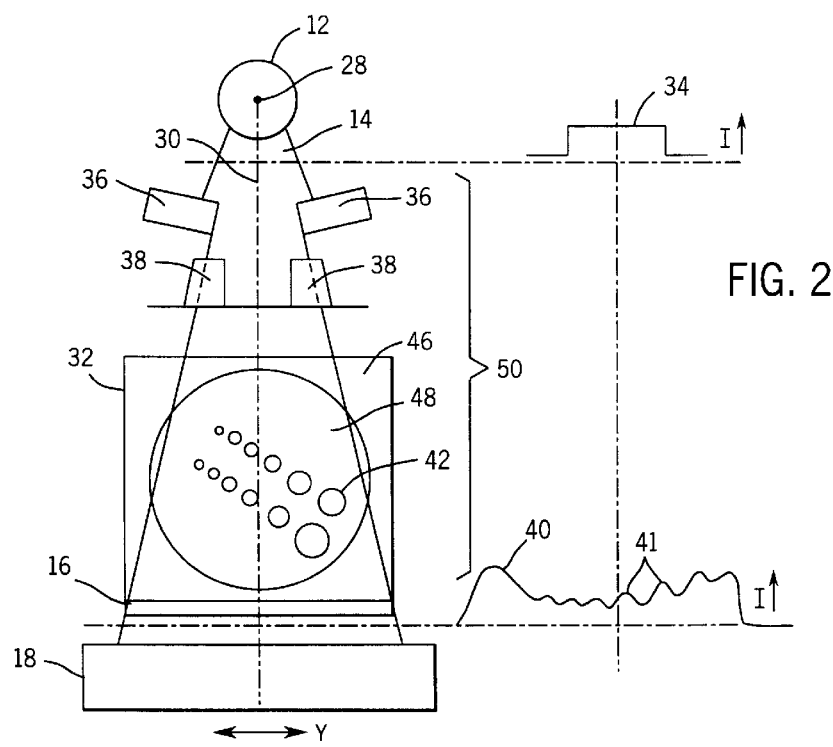
FIG. 2 is a schematic representation of the radiation therapy system of FIG. 1 showing the path of the radiation through a collimator, attenuating blocks and a phantom to a portal imaging device and showing the beam fluence profile and portal image.

Referring to FIG. 1, a radiation therapy system 10, suitable for use in the present invention, includes a radiation source 12 producing a radiation beam 14 directed across a patient support table 16 that may hold a patient (not shown) or a calibration phantom 32 (shown in FIG. 2). The radiation beam 14 may be a megavoltage x-ray beam (e.g., 6–10 megavolts) or other photon source suitable for radiation therapy. The radiation beam 14, as shown, is collimated to a fan shape; however, the invention is equally applicable to "cone beams" of radiation.

After passing through the patient support table 16 and either the patient or a calibration phantom 32, the beam 14 is received by an electronic portal imaging device (EPID) 18 having a detector surface 19 corresponding to the cross-sectional area of the beam 14. EPID 18 produces electronic signals providing measurements of the dose of the radiation received at a detector surface 19 at regularly spaced positions over the detector surface 19. Thus, the portal imaging device 18 generally provides the data of a projection image through the patient or phantom 32 along an axis of the radiation beam 14 at an arbitrary angle.

The EPID 18 may be a liquid-filled ionization chamber matrix such as is manufactured by Varian & Associates, San Jose, Calif., which generally provides a detector surface 19 composed of two circuit boards (not shown) containing 256 wires arranged at right angles to each other. The circuit boards are separated by a one millimeter thick layer of trimethylpentane which serves as an ionization medium. The circuit boards and ionization medium effectively create matrix ion chambers with 256 rows and 256 columns. Each such chamber has dimensions of 1.27 mm×1.27 mm×1 mm.

Radiation from beam 14 passing through the ion chambers ionizes the trimethylpentane. This ionization is detected by biasing one wire of one circuit board passing in the X-direction and scanning the remaining 256 wires in the Y-direction to detect charge with an electrometer. This process is repeated for each X-wire in turn and then the whole process is repeated again several times to improve the signal/noise ratio. It has been determined that the signal generated is almost entirely proportional to the square root of the dose rate for the individual detector.

It will be understood that the EPID 18 may alternatively be a film system in which an image is acquired with standard radiographic film, with filtration to expose the film in its linear region, with the film scanned with an electronic scanner to provide essentially the same data as provided directly by the EPID 18 to the computer 20. In both cases it is important that the EPID 18 be able to accurately measure dose.

The EPID 18 and radiation source 12 are mounted in opposition about the patient support table 16 on a rotating gantry 26. The patient support table 16 may be tipped so that, together with rotation of the gantry 26, the beam 14 may be directed at the patient or phantom 32 from a variety of angles as is understood in the art.

The signals from the EPID 18 are transmitted to a computer 20 where it is converted into a matrix of digital values; the values indicate the dose of radiation at each point of the detector surface 19. Computer 20 includes a display terminal 22 for displaying images and text and a keyboard 24 for user entry of data such is well known in the art.

A projection image derived from the matrix of digital values may be displayed on the terminal 22 of the computer 20. This projection image differs from a low energy x-ray image because tissues attenuate megavoltage x-ray differently than they attenuate low energy x-rays such as are typically used for imaging.

Referring now also to FIG. 2, the beam 14 of radiation diverges from a focal point 28 within the radiation source 12 and is directed generally along a radiation axis 30 toward a phantom 32 (or patient not shown in FIG. 2) resting on top of the patient's support table 16. Ideally, the beam 14, as emitted from the radiation source 12 with coarse collimation (not shown) has an essentially uniform beam fluence profile 34 referring to its intensity throughout its cross-sectional area, measured in a plane perpendicular to the axis 30.

In practice, the beam fluence profile 34 will deviate from perfect uniformity, even after the interposition of a flattening filter and other adjustment of the radiation source 12 known to those of ordinary skill in the art. For this reason, as will be described below, it is typical to make measurements of phantoms 32 in the beam 14 to account for any non-uniformity.

Beam 14 is next collimated by collimator blocks 36 which determine the outline of the beam that will ultimately be received by the patient or phantom 32. Collimator blocks 36 are radio-opaque and may be used, for example, to match the beam width to the outline of a tumor.

The collimated radiation beam 14 is next received by wedges 38 which serve to reduce the intensity of certain rays within the radiation beam 14 as is well understood in the art. The wedges 38 are placed so as better to control the desired dose to particular areas of the patient during radiation treatment and to compensate for varying thicknesses of the intervening tissue of the patient. As shown in FIG. 2, wedges 38 decrease the intensity of the edge rays of the beam 14 that pass through portions of the phantom 32 where the phantom is substantially thinner as might be desired to reduce dose to these areas in a human patient.

The rays of the beam 14 next pass through a phantom 32. The phantom 32 consists of a radio-lucent support structure 46 of polystyrene supporting a water-filled hollow plastic cylinder 48. Within the cylinder 48 are air filled tubes 42 of varying diameter. The tubes 42 provide a measure of resolution in a resulting portal image 40 to be described. Generally the phantom is intended to mimic certain properties of the human body. A variety of different phantoms such as are well known in the art, may be used in place of the phantom herein described, provided their geometry and composition may be accurately characterized.

After the radiation of the beam 14 exits the phantom 32, it may be recorded as a portal image 40, the portal image 40 being the measure of the dose of the beam 14 throughout its cross-sectional area in a plane perpendicular to the axis 30 after exiting the patient or phantom 32.

As depicted, even with wedges 38, the intensity of the rays of the radiation beam 14 at the edges of the beam 14 are greater than the central rays as a result of the difference in pathway length through the attenuating medium of the phantom 32. Ripples 41 in the portal image 40 are caused by the cylindrical air cavities 42 within the water phantom 32.

Generally, it should be noted that the portal image 40 has no sharp edges, such as might be expected from what is essentially shadows of the structure of the phantom 32. The reason for this is that substantial scattering of radiation in the phantom 32 causes a blurring of the portal image 40. It is known in the prior art to use the portal image 40 to verify the geometric placement of the collimator blocks 36 and wedges 38. In this application, scatter-induced blurring of the portal image 40 is undesirable.

Determining Dose Profiles

During a typical radiation treatment session, a tumor or the like within a patient will be treated with the radiation beam 14 directed at a variety of different angles about the patient. In order that dose received by the patient be correct in amount and location, it is necessary that characteristics of the radiation therapy system 10 be well-known. To this end, it is typical to collect a set of dose profiles within the volume of a water box and with the beam 14 collimated to different widths and with different radiation filters inserted at different positions within the collimated beam 14.

Dose profiles for one combination of collimation and attenuation are not easily predicted from the dose profiles, other combinations of collimation and attenuation. For example, changing the collimation of the beam 14 by moving the collimator blocks 36 together, decreases the dose at the center of the phantom 32 even if the center is at all times exposed directly to radiation. This decrease in center dose is caused in part by a decrease in scatter from the edges of the phantom now blocked by the collimator. Accounting for the effects of scatter previously required, that different dose profile measurements be made for each combination of collimation and attenuation. These repeated measurements, each which requires that an ionization probe be manually swept through the volume of the phantom, are expensive and time-consuming.

The present invention reduces the need for manual dose profiling by accurately modeling scatter, and based on a complete knowledge of the beam fluence profile 34, the properties and positions of the collimator blocks 36, the wedges 38 and the components of the phantom 32, calculating dose profiles within the phantom 32.

Important to this method is an accurate characterization of the actual beam fluence profile 34 indicating the fluence or intensity of the radiation beam 14. The present invention determines the beam fluence profile 34 by using the dose information contained in the portal image 40. The radiation beam 14 characterized by the portal image 40 is effectively transformed backwards through the phantom 32, the wedges 38 and the collimator blocks 36 to provide the beam fluence profile 34.

Figure 3:
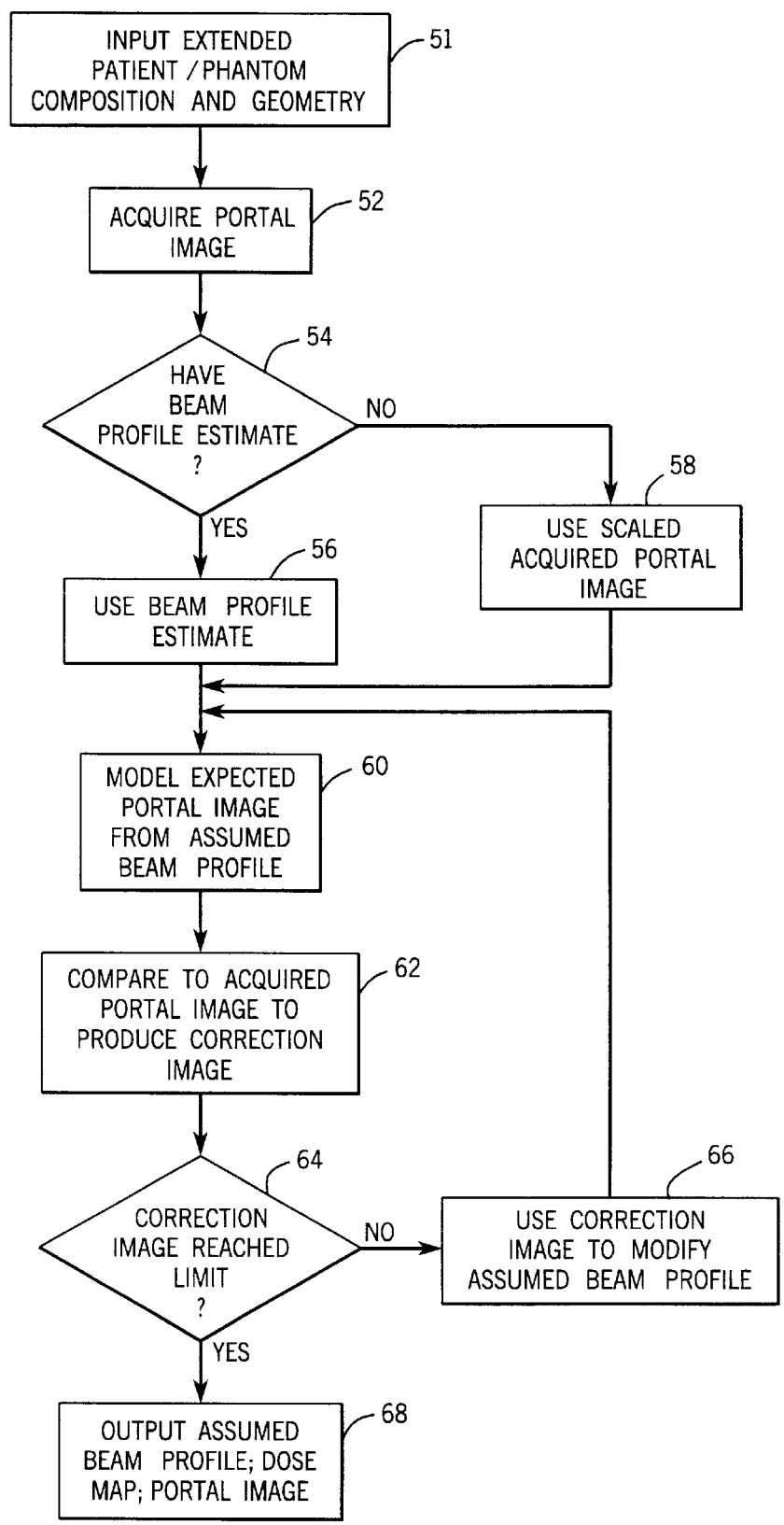
FIG. 3 is a flowchart describing the method of the present invention to determine beam intensity, dose distribution and a scatter-less portal image from a measured portal image.

Referring now also to FIG. 3, the first step of the present invention, represented by process block 51, is obtaining an accurate characterization of the extended phantom 50 comprising the attenuating material contained between the radiation source 12 and the EPID 18 and including the collimating blocks 36 and the wedges 38, the phantom 32 and the intervening spaces of air. Sufficient data must be collected to permit accurate determination of the type and amount of material along the path of an arbitrary ray from the radiation source 12 to EPID 18. Generally, because blocks 36, and wedges 38 and phantom 32 have regular geometries and well-known materials from which they are constructed, the properties of this extended phantom 50 may be readily determined.

This patient phantom 50 may be stored in the memory of computer 20 as a three dimensional matrix of data element, the value of each element identifying the properties ($\mu/\rho$) of the material through which a ray of radiation would be passing at a point in the extended phantom 50 and the location of the data element in the matrix defining the location of the point in the space of the extended phantom 50.

At process block 52, a portal image 40 is acquired of the extended phantom. Because radiation wholly blocked by the collimator blocks 36 cannot be evaluated by the portal image 40, this portal image 40 is best obtained with the collimator blocks 36 opened to their greatest extent as used in practice. The portal image 40 may be acquired with the EPID 18 or with film as has been previously described.

At decision block 54, it is next determined whether there is an estimate of the beam fluence profile 34. Normally, the estimate will simply be that the beam fluence profile is uniform throughout its cross-section as will be an adequate approximation with a recently adjusted radiation source 12.

If the beam fluence profile is known, the method proceeds to process block 56 and that beam fluence profile estimate is used for the later steps. In those circumstances where the beam fluence profile 34 is not known, for example, when the radiation source 12 produces a beam that deviates significantly from uniform or where there is unknown or hard-to-characterize filtration placed within the beam 14, at process block 58 the portal image 40 forms a basis for the beam fluence profile estimate. In this case, the portal image 40 is compressed along the Y-axis based on the normal divergence of the radiation beam 14 and expanded in intensity according to the inverse square law of intensity which diverging radiation beams obey. The effect of the attenuating material of the extended phantom 50 may also be taken into account in this adaptation of the portal image 40 as an estimate of the beam fluence profile 34.

At process block 60, the estimated beam fluence profile from either process block 56 or process block 58 is used at process block 60 to model an expected portal image 40 based on knowledge of the extended patient/phantom obtained at process block 51. Two approaches to this modeling are described below but importantly both provide an estimate for scattering of radiation caused by the extended phantom 50.

At process block 62, the modeled portal image is compared to the actual portal image 40 acquired at process block 52 and a correction image, being a point by point subtraction of these two portal images is obtained. Each point in the correction image is equal to the difference between the corresponding two points in the modeled and actual portal images at a similar location.

Alternatively at process block 62 a ratio of the actual portal image 40 acquired at process block 52 to the modeled portal image on a point by point basis may be obtained. Each point in the correction image is then equal to the ratio between the corresponding two points in the actual and modeled portal images at a similar location.

At decision block 64, if this correction image is of uniformly low intensity (or nearly one in the ratio version), indicating that the modeled portal image and the actual portal image are nearly equal, the process is complete and at process block 66, the estimated beam fluence profile, from which the modeled portal image is derived, is assumed to accurately represent the true beam fluence profile 34 of the radiation therapy system 10. A single FIGURE measuring convergence between the two portal images may be obtained by summing the square of each point in the correction image and comparing this sum to a predetermined threshold.

Typically, in a first iteration, the correction image will not be of uniformly low magnitude but will indicate considerable difference between the actual portal image and the portal image derived from an assumed beam fluence profile. In this case, the correction image is backprojected or scaled according to the known divergence of beam 14 and by the known attenuating effects of the material of the extended phantom 50 along rays between each point in the correction image and the radiation source 12. The scaled correction image is then subtracted from the estimated beam fluence profile (or multiplied by the estimated beam fluence profile for the ratio version). This subtracting of the correction image from the assumed beam fluence profile is represented at process block 66.

Thus, using the portal image 40 and the modeled portal image and the estimated beam fluence profile, the next estimated beam fluence profile may be obtained in such a way as to cause the iterative processes to converge to a solution which will accurately predict the measured exit dose or portal image 40. When this occurs, a accurate determination of the actual primary energy fluence in the volume has been obtained-within the accuracy of the modeling and the characterization of the phantom.

The method then loops back to process block 60 and the new estimated beam fluence profile, as modified by the correction image, is again used to model an expected portal image. Process blocks 62 and 64 are repeated for an arbitrary number of times until the modeled portal image converges to equal the actual portal image 40 or else convergence cannot be obtained under a certain number of repetitions.

In this latter case, the operator is signaled that convergence has not been achieved which normally indicates an error in the characterization of the extended phantom 50 as obtained at process block 51. This error will be significant in the imaging of a patient, to be described, as it may indicate that the patient is not properly positioned.

Otherwise at process block 66, the estimated beam fluence profile is taken as the actual beam fluence profile 34.

Therefore, although generally scattered radiation cannot be uniquely unscattered to transform the portal image to the beam fluence profile, the iterative process so described provides a method of obtaining a good estimate of the beam fluence profile 34 from the portal image 40. It will be noted, although this process is iterative, only one portal image 40 need be obtained and the iteration may be done within software without additional external data collection steps.

As will be understood to those of ordinary skill in the art, the steps of FIG. 3 may be performed by software running on computer 20 augmented by inputs of necessary data from the user at certain stages.

Referring to process block 68, once the beam fluence profile 34 is accurately characterized, the dose map may be produced of dose within the phantom 32 for a variety of configurations of blocks 36 and wedges 38 using the same modeling used in process block 60 as will be described below. Further, once the beam fluence profile 34 is accurately characterized, the attenuation of the phantom may be modeled without scatter so as to extract an extremely sharp portal image from the original portal image 40 as may be preferable for verifying certain geometrical aspects of the radiation therapy system 10.

In a second embodiment, the same approach may be used not with the phantom but with a patient. In this case, the patient is characterized by a x-ray tomographic image or the like.

Calculation of Expected Portal Image

Monte Carlo Modeling

One method of modeling the expected portal image per process block 60 is the Monte Carlo method. In this method, large numbers of photons are individually modeled and tracked through the extended phantom 50. Their combined effect upon reaching the EPID 18 provides the expected portal image.

In this process, randomly directed photons within the beam 14, having an energy defined by the energy of the megavoltage x-rays and in number proportional to the intensity of the beam fluence profile along a given ray of the beam 14 are tracked through the extended phantom 50. The tracking requires that at regular intervals along the photon's path, the probability of interaction with the material of the extended phantom 50 is determined based on knowledge of that material of the extended phantom. A properly constrained random number generator is then used to select a new path direction and photon energy based on the known physics of photon scattering. If the photon energy is not below a predetermined cut-off value (i.e., the photon is not absorbed), modeling is continued along this new path with the probability of interaction again at regular intervals along the pathway until the photon exits the patient and is received by the EPID 18, it is absorbed or its passes out of bounds, indicating that it will not ultimately be received by the EPID 18.

At each site of interaction, an electron ejected by the photon along a different path determined by the interaction of the photon, is also modeled. Like the photon, the probability of interaction with the material of the extended phantom 50 is determined based on knowledge of that material of the extended phantom. A properly constrained random number generator is then used to select a new path direction and electron energy based on the known physics of electron scattering. Dose is accumulated for each element of the extended phantom 50 along the path of the electron.

The electrons ejected by photons arriving at the EPID 18 are counted to produce a modeled portal image 40.

TERMA/Scatter Kernel Modeling

This Monte Carlo method, with evaluation of a suitably large number of photons and electrons and a suitably fine scale of evaluation of their interaction, can provide an accurate model of the expected portal image. Unfortunately, the method has the drawback of being computationally intensive and is thus time consuming. A far more computationally efficient algorithm determines total energy release per mass (TERMA) throughout the extended phantom 50 and uses precomputed dose deposition kernels representing the scatter of the photons and electrons. These kernels may in fact be precomputed with the Monte Carlo technique. The superposition/convolution of the kernels provides the effective spreading of dose from a single terma interaction site as is caused by scattering.

Computation of Dose Profile from Beam Fluence Profile

Before describing the procedure for computing the expected portal image, the method of computing dose to the extended phantom 50, taking into account scatter, will be described.

Figure 4:
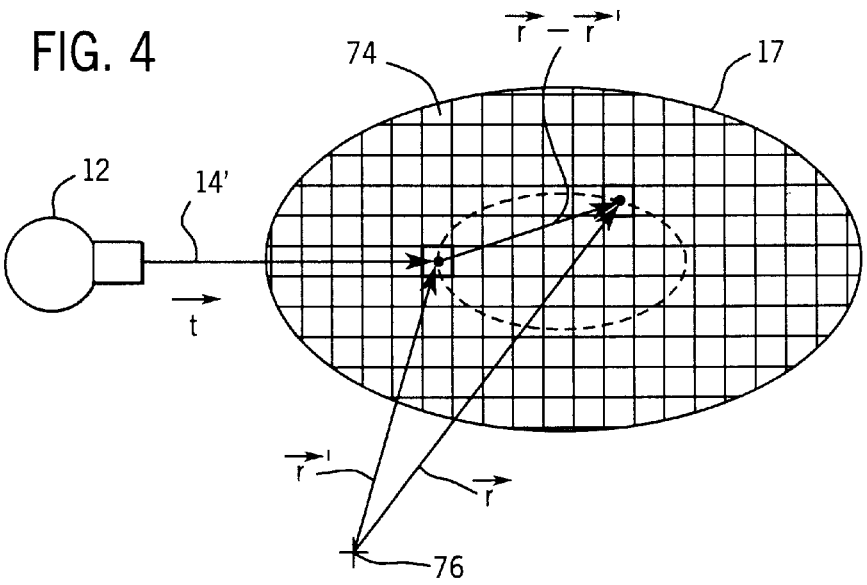
FIG. 4 is a diagrammatic representation of a patient receiving radiation therapy, showing the scatter kernel and the coordinate system used to describe the present invention.

Referring to FIG. 4, each voxel 74 of the patient 17 may be identified by a vector $\vec{r}$ defined from a given reference point 76. The dose at each voxel 74 is $D(\vec{r})$. Generally, the dose at any voxel $\vec{r}$ will depend on the energy received at that voxel $\vec{r}$ from radiation scattered from adjacent voxels $\vec{r}\,'$ (where adjacent voxels $\vec{r}\,'$ include the voxel $\vec{r}$, i.e., the radiation received directly from the radiation source 12). The dose $D(\vec{r})$ for a given voxel $\vec{r}$ is given by the following formula:

$$D(\vec{r}) = \int T(\vec{r}\,')A(\vec{r}-\vec{r}\,')d^3\vec{r}\,' \tag{1}$$

where $T(\vec{r}\,')$ is a value indicating the magnitude of the primary total energy released at $\vec{r}\,'$ per unit mass of that voxel $\vec{r}\,'$ and is called the "terma" (total energy released per unit mass).

For a monoenergetic external radiation source, the terma rate $\dot{T}(\vec{r})$ is described by:

$$\dot{T}(\vec{r}\,') = \frac{\mu}{\rho}(\vec{r}\,')E\phi(\vec{r}\,')dt \tag{2}$$

where $$\frac{\mu}{\rho}$$

is an effective mass attenuation value at the voxel $\vec{r}\,'$, E is the energy of the radiation photons in Joules, $\phi$ is the distribution of the fluence rate (flux density). The value of $\mu/\rho$ may be deduced from the tomographic scan data collected by means of a tomographic imaging system or by a priori knowledge about the construction of the phantom 32.

The integration of energy times fluence rate over time is energy fluence $\Psi(\vec{r}\,')$ where:

$$\Psi(\vec{r}\,') = E\int\phi(\vec{r}\,')dt \tag{3}$$

hence $$T(\vec{r}') = \frac{\mu}{\rho}(\vec{r}')\Psi(\vec{r}') \quad (4)$$

Equation (4) basically relates how much energy from the ray within beam 14 interacts with the voxel r'.

Terma may be computed for each volume element of the extended phantom 50 by following along straight rays from the radiation source 12 to the EPID 18 and assigning each voxel a terma based on the intensity of the radiation following that ray and the exponential attention caused by the intervening volume elements and their values of $\mu/\rho$ for those volume elements. The decrease in fluence caused by the inverse square law and beam hardening effects are also taken into account.

The scattering kernel $A(\vec{r} - \vec{r}')$ is a convolution kernel describing non-stochastic energy transport or scattering in a uniform medium. $A(\vec{r} - \vec{r}')$ thus describes how the energy from each voxel $\vec{r}'$ spreads to contribute to the dose at voxel $\vec{r}$.

The kernel $A(\vec{r} - \vec{r}')$ may be generated using a Monte Carlo method as is generally understood in the art. As mentioned, it is a three-dimensional function indicating the fraction of energy absorbed at voxel $\vec{r}$ per unit of energy released at voxel $\vec{r}'$. The energy emitted from the terma of each voxel $\vec{r}'$ finds it source in a directed ray within beam 14 from external radiation source 12 and thus $A(\vec{r} - \vec{r}')$ is generally anisotropic as suggested in FIG. 5, spreading outward away from the entry of within beam 14. Energy conservation requires that:

$$\int A(\vec{r}')d^3\vec{r}' = 1.0 \quad (5)$$

That is, if the energy transferred by the primary interaction were all deposited on the interaction point, the kernel would be approximated as a delta function.

Figure 5:
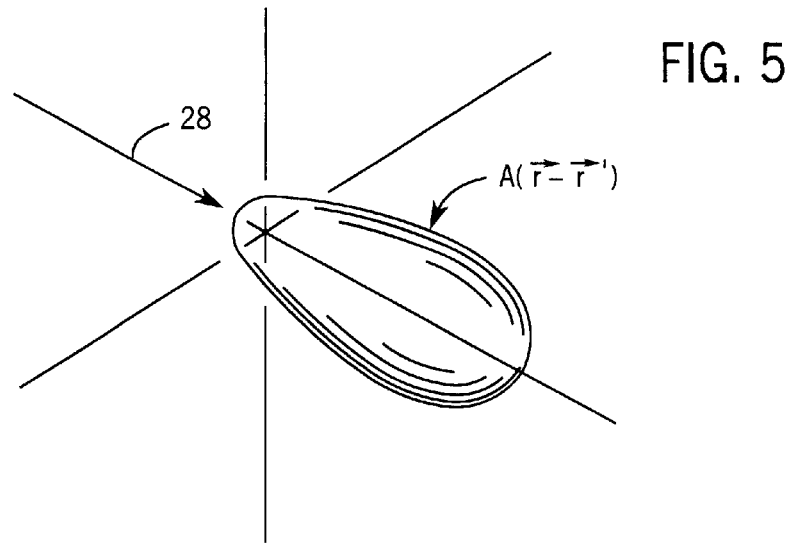
FIG. 5 is a perspective representation of a monodirectional scatter kernel associated with a radiation beam at a defined angle.

Referring still to FIG. 5, dose may be computed by superimposing the kernels for each of the sites of energy released. Rays within the kernels are scaled in proportion to a "radiological distance" rather than the geometric distance to handle tissue heterogeneity. This scaling modifies the scatter to accurately reflect the medium through which the electrons travel and in particular to permit the inclusion of air gaps in the computational volumes. This ability to modify the dose and scatter treatment to reflect the underlying material allows extension of the computational area to the extended phantom as is required for the present method.

Unlike the Monte Carlo method, the terma method described above allows for the effect of scatter only in the kernel which accurately models only the first generation of scattered photons and provides a reasonable estimate from higher orders of scatter. This simplification is acceptable because the first generation of scattered photons account for most of the observed scatter.

The dose image at the EPID 18 then is the result of the terma computed at the EPID 18 with the superimposed kernel on that terma together with the effect of upstream kernels from terma higher in the extended phantom. Generally the kernel may extend on the order of 60 cm as a result of the scaling of the terma by radiological distance as has been described.

The above description has been that of a preferred embodiment of the present invention. It will occur to those who practice the art that many modifications may be made without departing from the spirit and scope of the invention. In order to apprise the public of the various embodiments that may fall within the scope of the invention, the following claims are made.

We claim:

1. A system for verifying radiation delivered to an object, the system comprising:
    a radiation source with an output beam directed to the object;
    detector means for sensing radiation output from the output beam and for generating exit radiation signals, the detector means sensing the output radiation beneath the object; and
    processing means for calculating the radiation delivered to the object, the processing means using the exit radiation signals from the detector means for the calculation.

2. The system for verifying radiation delivered to an object of claim 1, wherein the processing means is capable of generating a delivered radiation map, the delivered radiation map being reverse calculated, the reverse calculation being based on the exit radiation signals from the detector means and attenuation factors of the object.

3. The system for verifying radiation delivered to an object of claim 2, further comprising output means for outputting the delivered radiation map during delivery of the radiation.

4. The system for verifying radiation delivered to an object of claim 3, wherein the output means is at least one of a monitor and a printer.

5. The system for verifying radiation delivered to an object of claim 2, wherein the processing means displays the delivered radiation map in a two dimensional manner.

6. The system for verifying radiation delivered to an object of claim 2 wherein the attenuation factors of the object are based on a tomographic image of the object.

7. The system for verifying radiation delivered to an object of claim 2 wherein the reverse calculation accounts for radiation scatter caused by the object.

8. The system for verifying radiation delivered to an object of claim 1, wherein the detector means is located in a portal imaging system arranged beneath the object.

9. A method for verifying radiation delivered to an object, the object containing a field to be irradiated, the method comprising the steps of:
    generating an initial output beam of radiation from a radiation source, the initial output beam being directed toward the field on the object;
    sensing exit radiation from the initial output beam directed towards the field, the sensing occurring after the radiation passes through the object; and
    calculating the derived output beam, the derived output beam being at least in part based on the sensed exit radiation.

10. The method for verifying radiation delivered to an object of claim 9, further comprising the step of generating exit radiation signals, the exit radiation signals corresponding to the sensed exit radiation.

11. The method for verifying radiation delivered to an object of claim 10, wherein the calculating of the derived output beam is at least in part based on the exit radiation signals and attenuation factors of the object.

12. The method for verifying radiation delivered to an object of claim 11 further comprising the step of obtaining a tomographic image of the object and determining the attenuation factors of the object from the tomographic image.

13. The method for verifying radiation delivered to an object of claim 9, further comprising the step of outputting a radiation map, the radiation map including information from at least one of the derived output beam and a planned radiation dose.

14. The method for verifying radiation delivered to an object of claim 13, further comprising the step of displaying the radiation map.

15. The method for verifying radiation delivered to an object of claim 12, further comprising the step of displaying the radiation map on at least one of a monitor and a printer, the displaying occurring when radiation is being delivered to the object.

16. The method for verifying radiation delivered to an object of claim 9 wherein the calculation of the derived output beam accounts for scatter of the radiation by the object.

17. A system for verifying radiation delivered to an object, the system comprising:

a radiation source with an output beam directed to the object;

intermediate means for temporally modulating the output beam;

detector means for sensing radiation output from the output beam as modified by the intermediate means and for generating exit radiation signals, the detector means sensing the output radiation beneath the object; and processing means for calculating the radiation delivered to the object, the processing means using the exit radiation signals from the detector means for the calculation.

18. The system for verifying radiation delivered to an object of claim 17, wherein the processing means is capable of generating a delivered radiation map, the delivered radiation map being reverse calculated, the reverse calculation being based on the exit radiation signals from the detector means and attenuation factors of the object.

19. The system for verifying radiation delivered to an object of claim 18, further comprising output means for outputting the delivered radiation map during delivery of the radiation.

20. The system for verifying radiation delivered to an object of claim 19, wherein the output means is at least one of a monitor and a printer.

21. The system for verifying radiation delivered to an object of claim 18, wherein the processing means displays the delivered radiation map in a two dimensional manner.

22. The system for verifying radiation delivered to an object of claim 18 wherein the attenuation factors of the object are based on a tomographic image of the object, and wherein the intermediate means includes at least one of a set of wedges and a set of collimator leaves that can be adjusted over time to temporally modulate the output beam.

23. The system for verifying radiation delivered to an object of claim 18 wherein the reverse calculation accounts for radiation scatter caused by the object.

24. The system for verifying radiation delivered to an object of claim 17, wherein the detector means is located in a portal imaging system arranged beneath the object.

25. A method for verifying radiation delivered to an object, the object containing a field to be irradiated, the method comprising the steps of:

generating an initial output beam of radiation from a radiation source, the initial output beam being directed toward the field on the object;

modifying the initial output beam before the initial output beam impinges the object, wherein the modifying can be temporally modulated;

sensing exit radiation from the initial output beam directed towards the field, the sensing occurring after the radiation is modified and passes through the object; and calculating the derived output beam, the derived output beam being at least in part based on the sensed exit radiation.

26. The method for verifying radiation delivered to an object of claim 25, further comprising the step of generating exit radiation signals, the exit radiation signals corresponding to the sensed exit radiation.

27. The method for verifying radiation delivered to an object of claim 26, wherein the calculating of the derived output beam is at least in part based on the exit radiation signals and attenuation factors of the object.

28. The method for verifying radiation delivered to an object of claim 27, further comprising the step of outputting a radiation map, the radiation map including information from at least one of the derived output beam and a planned radiation dose.

29. The method for verifying radiation delivered to an object of claim 28, further comprising the step of displaying the radiation map.

30. The method for verifying radiation delivered to an object of claim 28, further comprising the step of displaying the radiation map on at least one of a monitor and a printer, the displaying occurring when radiation is being delivered to the object.

31. The method for verifying radiation delivered to an object of claim 27 further comprising the step of obtaining a tomographic image of the object and determining the attenuation factors of the object from the tomographic image.

32. The method for verifying radiation delivered to an object of claim 27 wherein the calculation of the derived output beam accounts for scatter of the radiation by the object.

* * * * *

UNITED STATES PATENT AND TRADEMARK OFFICE
CERTIFICATE OF CORRECTION

PATENT NO.    : 6,636,622 B2
DATED         : October 21, 2003
INVENTOR(S)   : Mackie et al.

It is certified that error appears in the above-identified patent and that said Letters Patent is hereby corrected as shown below:

Column 1,
Line 5, please add the following:
--
                STATEMENT REGARDING FEDERALLY
             SPONSORED RESEARCH OR DEVELOPMENT
    This invention was made with United States government support awarded by the following agencies: NIH Grant Nos: CA52692; CA48902. The United States has certain rights in this invention. --

Signed and Sealed this

Twentieth Day of April, 2004

JON W. DUDAS
*Acting Director of the United States Patent and Trademark Office*